United States Patent [19]
Holtman

[11] 4,449,979
[45] May 22, 1984

[54] ABSORBENT STRUCTURE HAVING GRADIENT DENSITIES

[75] Inventor: Dennis C. Holtman, Orland Park, Ill.

[73] Assignee: Johnson & Johnson Baby Products Company, New Brunswick, N.J.

[21] Appl. No.: 181,539

[22] Filed: Aug. 26, 1980

[51] Int. Cl.$^3$ ............................................. A41B 13/02
[52] U.S. Cl. .................................................... 604/379
[58] Field of Search .................. 128/284, 287, 290 R; 604/358, 367, 374, 378, 379–380, 385

[56] References Cited

U.S. PATENT DOCUMENTS

| | | | |
|---|---|---|---|
| 3,430,629 | 3/1969 | Murphy | 128/284 |
| 3,545,441 | 12/1970 | Gravdahl | 128/287 |
| 3,592,194 | 7/1971 | Duncan | 128/287 |
| 3,848,598 | 11/1974 | Mesek | 128/287 |
| 3,965,904 | 6/1976 | Mesek et al. | 128/287 |

Primary Examiner—C. Fred Rosenbaum
Attorney, Agent, or Firm—Martha A. Michaels

[57] ABSTRACT

An absorbent structure of loosely compacted cellulosic fibers substantially rectangular in shape having increasing gradient densities from the central portion to each transverse end and methods for making the structure.

14 Claims, 7 Drawing Figures

ABSORBENT STRUCTURE HAVING GRADIENT DENSITIES

BACKGROUND OF THE INVENTION

The present invention relates to an absorbent structure containing loosely compacted cellulosic fibers, which structure is particularly suitable for use in absorbent products requiring a substantial liquid holding capacity.

Absorbent structures such as disposable diapers, sanitary napkins, incontinent pads and the like are generally structured so as to have a facing sheet which is moisture permeable, an absorbent batt which has a high liquid holding capacity and a backing sheet which is moisture impervious. For any absorbent structure to be satisfactory, it is highly desirable for the structure to (1) readily accept liquid (2) easily transport the liquid from one portion of the structure to another and (3) hold the liquid accepted. The facing sheet mentioned above must permit the liquid to penetrate the facing to reach the absorbent batt. The backing sheet keeps the liquid from leaking and therefore must be moisture impermeable. The present invention relates to an improvement in the absorbent batt used for these absorbent structures.

Conventionally, loosely compacted cellulosic fibrous batts are of substantially rectangular shape and are made by air laying wood pulp fibers, cotton linters or the like, on a foraminous support. The batt may be laid in a prescribed shape or may be shaped subsequent to the air laying of the fibers. These batts are incorporated by various techniques into products such as disposable diapers, sanitary napkins, incontinent pads and the like. Various techniques have been developed or suggested for improving the absorbent characteristics of the absorbent batts and to improve the liquid transporting characteristics, i.e., wicking characteristics. For instance, U.S. Pat. No. 3,017,304 to Burgeni teaches forming a paper-like densified skin on one surface of the absorbent batt. The skin assists in transporting the liquid and lends integrity to the batt. In another instance, U.S. Pat. No. 3,938,522 to Repke suggests densifying portions of the batt to both assist in transporting of liquid and strengthening the absorbent batt. Previously, in each instance when a portion or portions of the absorbent batt have been densified, liquid holding capacity has been reduced and those densified portions are rigid and have a tendency to break when the batt is flexed. As mentioned above, for any absorbent structure to be satisfactory, it is not only necessary for the structure to hold liquid, but also to readily accept liquid and transport it. The liquid holding capacity of the absorbent structure relates to the pore size of the fibrous bed. If the pore size (i.e., the spaces surrounding the fibers) is large, then the structure will have a relatively high liquid holding capacity but generally does not accept and transport liquid readily. On the other hand, if the pore size is smaller, the structure readily accepts and wicks liquid but may have a lower liquid holding capacity.

SUMMARY OF THE PRESENT INVENTION

It has been discovered that a flexible absorbent batt can be made from loosely compacted, cellulosic fibers such as wood pulp fibers, which will readily accept and wick liquid while retaining a high liquid holding capacity.

The present invention provides an absorbent structure comprising an absorbent batt substantially rectangular in shape and having gradient densities whereby the density of the batt increases from the center to the transverse ends.

The new absorbent structure is made by air laying cellulosic fibers to form a batt and subjecting the batt to compression in a contoured press, or by calendaring at different pressures. The pressure increases from the central region to the transverse ends of the batt.

DETAILED DESCRIPTION OF THE PRESENT INVENTION

The "wicking" of liquid is the transporting of liquid from one point to another in an absorbent structure. Wicking has heretofore been accomplished by densifying either one surface of an absorbent batt or by embossing lines in a prescribed pattern in a selected area to create a smaller capillary structure resulting in an increased capillary pressure. One method of densifying an area is disclosed in U.S. Pat. No. 3,017,304 wherein a "paper-like" skin is formed on one surface of an absorbent batt. Another method of densifying a selected area of fibers is found in U.S. Pat. No. 3,938,522 wherein densified regions are provided.

In these absorbent structures wherein a portion of the fibrous batt is densified to decrease the capillary radius between adjacent fibers resulting in an ability to wick more liquid in a given period of time, the densified area does not hold as much liquid, resulting in a reduction of the liquid holding capacity of the absorbent structure. The present invention improves the wickability and integrity i.e., stability of the absorbent structure while retaining flexibility without a loss of liquid holding capacity.

The absorbent structure of the present invention is a fibrous batt formed of loosely compacted cellulosic fibers which are primarily held together by interfiber bonds requiring no added adhesive. In order for the absorbent structure to perform, the batt should be substantially wettable, should transport liquid from one area to another, and should have a high liquid holding capacity. It has been discovered that by providing an absorbent batt of substantially rectangular shape, having longitudinal sides longer than the transverse ends, and having gradient densities whereby the density of the batt increases from the center to the transverse ends, the objectives are reached.

It has further been discovered that such an absorbent structure is provided by forming a loosely compacted cellulosic batt having longitudinal sides longer than the transverse ends and compressing the batt in a contoured press or by calendaring at different pressures to provide gradient densities which increase from the center of the batt to the transverse ends.

Although the density of the absorbent batt increases along a longitudinal line from the central portion to each transverse end, the density in a cross direction is substantially constant on any given line.

It has been observed that the wicking of liquid from the central portion toward each transverse end is improved and even though the density in a cross direction is substantially constant on any given line, no side leakage is experienced. In other words, the structure of the present invention wicks longitudinally in preference to the cross direction, even though the structure is shorter from side to side.

Figure 1:
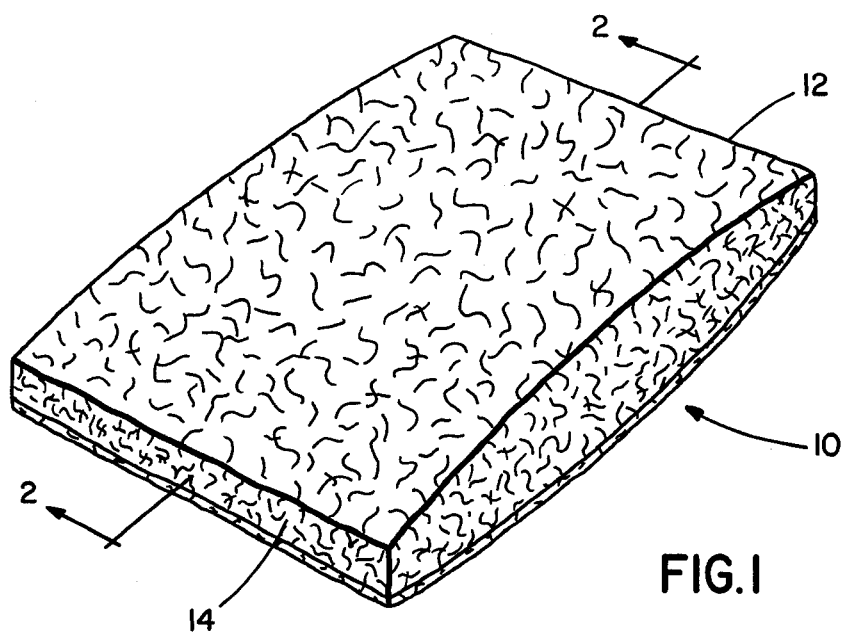
FIG. 1 is a perspective view of an absorbent structure of the present invention.
Figure 2:
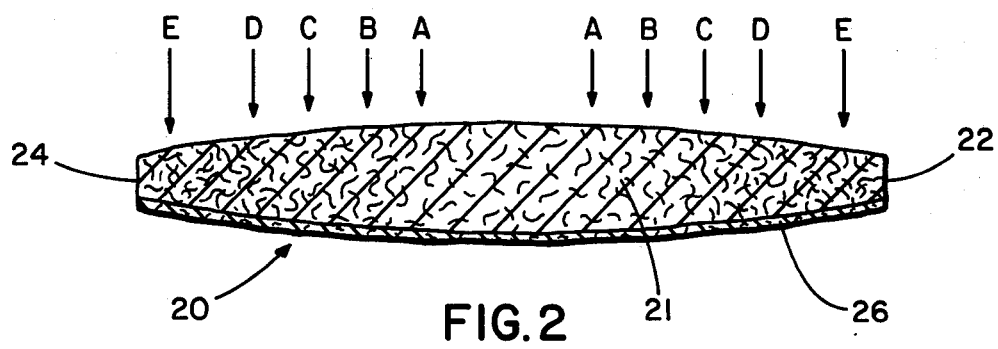
FIG. 2 is a cross-sectional view of the absorbent structure of FIG. 1 taken along lines 2—2.

In FIG. 1 an absorbent batt 10 is provided. The density of the batt 10 increases from the center of the batt toward each of the ends 12 and 14. For instance, in FIG. 2, a cross section of FIG. 1 at line 22, an absorbent batt 20 increases in density from the central portion to the transverse ends 22 and 24 in increments represented by the letters A, B, C, D, and E. The batt 20 consists of loosely compacted cellulosic fibers 21 and a paper-like densified skin 26. The skin 26 assists in providing stability to the batt and in wicking liquid from one portion of the batt 20 to another.

Figure 3:
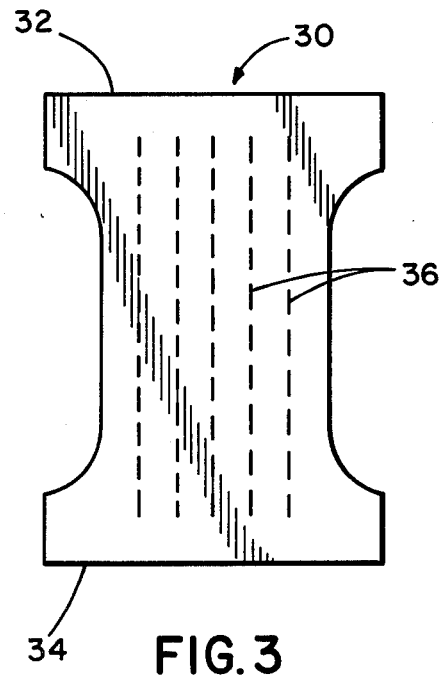
FIG. 3 is a top view illustrating a particular configuration of another embodiment of the present invention.

FIG. 3 illustrates one desirable shape of an absorbent batt 30 that is particularly suitable for use in a disposable diaper structure. The density of the fibrous structure increases from the central portion to each transverse end 32 and 34. Although cross direction wicking is not a problem, embossed lines 36 as provided may increase the speed of the wicking of liquid and additionally lend stability to the batt 30.

Figure 4:
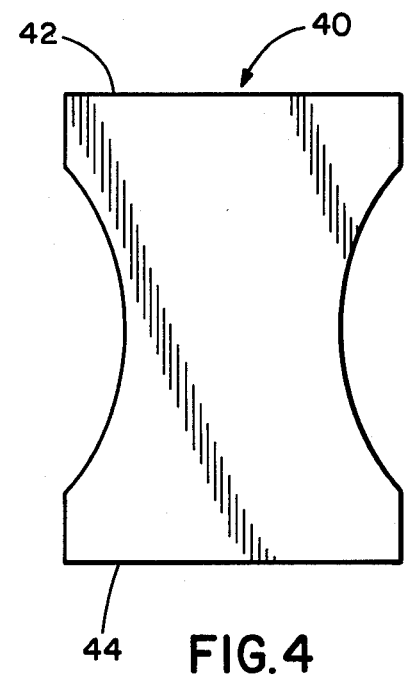
FIG. 4 is a top view illustrating still another particular configuration of an embodiment of the present invention.

FIG. 4 illustrates another shaped batt 40 suitable for use in a disposable diaper structure. The density of the batt 40 is increased from the central region to the transverse ends 42 and 44.

Figure 5:
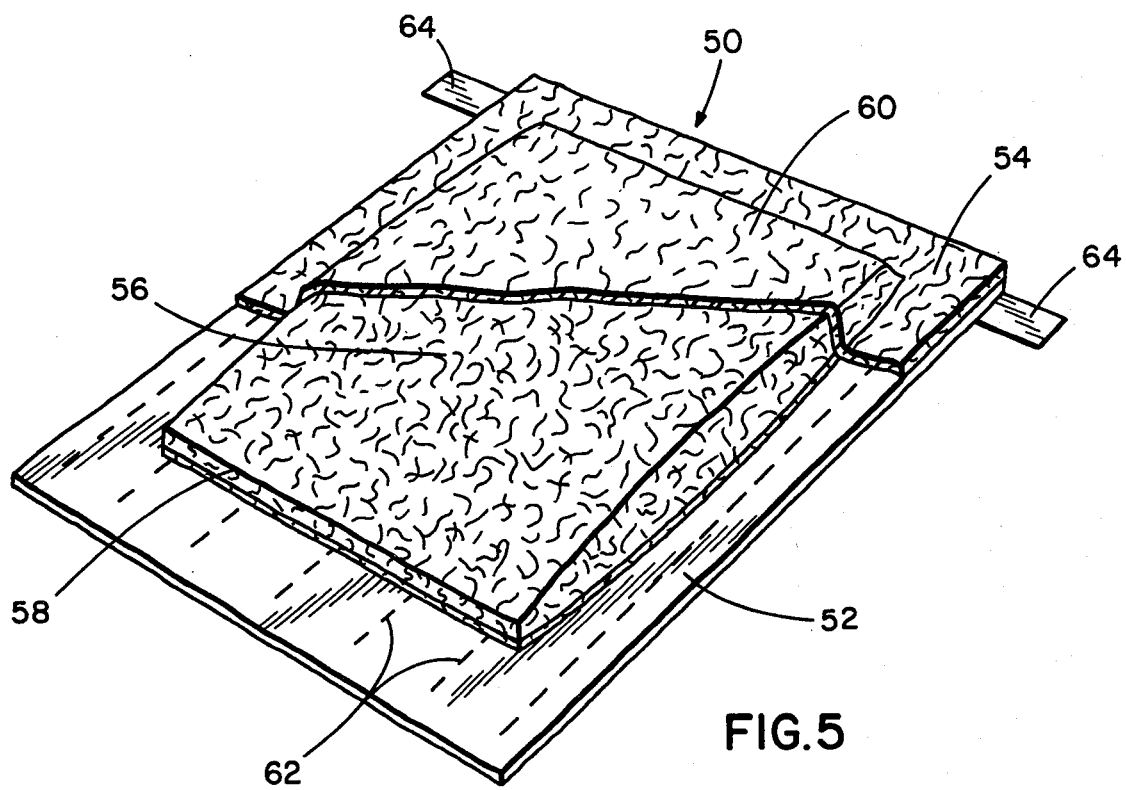
FIG. 5 is a perspective view with certain portions broken away for clarity of illustration of one embodiment of a diaper of the present invention.

FIG. 5 presents a typical disposable diaper structure 50 using the absorbent batt 56 of the present invention. A moisture-impermeable backing sheet 52 is laminated to a moisture-permeable facing 54 with the absorbent batt 56 held in place between the backing and the facing. The density of the batt 56 increases from the central region to each end 58 and 60. The batt 56 is held in place and the facing 54 and backing 52 laminated by glue lines 62. Tape tabs 64 are provided for securing the diaper about the waist of the infant.

Figure 6:
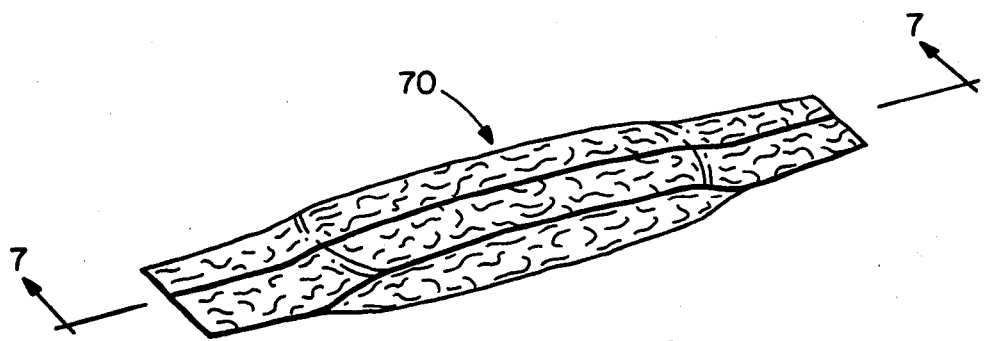
FIG. 6 is a perspective view of one embodiment of a sanitary napkin of the present invention.
Figure 7:
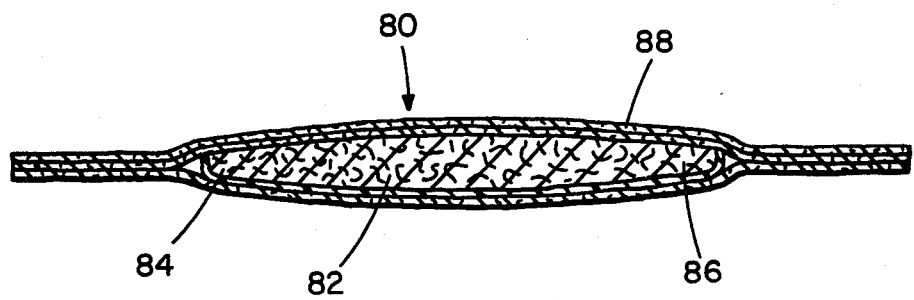
FIG. 7 is a cross-sectional view of the sanitary napkin of FIG. 6 taken along lines 7—7.

FIG. 6 depicts a sanitary napkin 70 containing an absorbent batt of the present invention. FIG. 7 illustrates the sanitary napkin of FIG. 6 taken along the line 7—7. The sanitary napkin 80 contains an absorbent batt 82 wherein the density increases from the central portion toward the transverse ends 84 and 86. The napkin is covered with a covering 88.

The absorbent batts of the present invention are prepared by forming a substantially uniform batt of air laid loosely compacted cellulosic fibers. The fibers generally are wood pulp fibers which have been subjected to conventional chemical processing. Typically chemically processed wood pulp fibers appear in ribbon-like form and upon air laying become entangled to provide a degree of cohesiveness and fibrous web integrity.

Non-delignified wood pulp fibers are also suitable and may have an additive present to enhance the cohesiveness of the fibers to form a stable absorbent batt.

Preferably, whether the batt is made from chemically processed fibers or non-delignified wood pulp fibers, the batt is provided with an integral, continuous, paperlike, densified, cellulosic fibrous layer increasing in density from the central region to each transverse end. This layer is generally located on the planar surface away from the point of entry of liquid when the product is in use. U.S. Pat. No. 3,017,304, Burgeni, describes the paper-like skin and a process for preparing an absorbent batt having a densified fibrous layer.

The air laid, loosely compacted absorbent batt is subjected to different degrees of compaction so that the central portion of the batt receives little or no compaction whereas the transverse ends of the batt are compacted sufficiently to provide a density generally at least 1.5 times that of the central portion. Portions of the batt between the central portion and the transverse ends are increasingly higher in density from the central portion to the ends. It is not necessary that the progression of the density between the central portion and each end be uniform or symmetrical. However, a continuing increase in density from the central portion to the ends is preferred.

The absorbent batts of the present invention are particularly useful in disposable products such as disposable diapers, sanitary napkins, incontinence pads and the like. Each of the disposable products usually contains a moisture-impermeable backing sheet, an absorbent batt in superposed position and a moisture permeable facing or cover in superposed position on the side of the batt opposite the backing sheet.

The disposable product when ideally constructed permits a void of liquid onto the facing to be rapidly drawn through the facing into the absorbent batt for storage. Leakage when the batt becomes substantially wetted is prevented by the backing sheet.

Because a void generally occurs in a relatively small area, it is necessary that the absorbent batts have the ability to transport or wick the liquid to more remote areas of the batt.

The absorbent batt is substantially more wettable than the facing and tends to draw liquid away from the facing. The individual fibers of the batt are extremely wettable, generally having liquid-fiber contact angles below about 15° and approaching zero in the optimum embodiment. The wickability of the body of the batt for liquid is limited by its low density which results in a large effective capillary radius for the capillaries between adjacent fibers.

The pressure causing a liquid to enter a cylindrical capillary is expressed by the equation:

$$P = (2v \cos \theta)/r$$

wherein

P is the capillary pressure $v$ is the surface tension of the liquid $\theta$ is the liquid-fiber contact angle, and r is the capillary radius.

With a given liquid, the pressure (capillary force) increases with the cosine of the liquid-fiber contact angle (reaching a maximum where the angle is zero), and increases with narrower capillary radii so that narrower capillaries will draw liquid from wider ones.

As the density gradient increases from the central portion of the absorbent structure to the transverse ends, the capillary pressure increases.

It has been noted that as the density of a fibrous absorbent structure increases the wickability of liquid from one area to another increases, but the overall liquid holding capacity decreases.

In the absorbent structure of the present invention, the density gradient features provide improved wicking but also greater liquid holding capacity than the same structure without the density gradient feature.

The following examples illustrate specific embodiments of the present invention, and are not limiting in any way.

EXAMPLE 1

Absorbent batts are formed by air laying wood pulp fibers from a hammermill onto a foraminous belt. The batts are shaped so as to resemble the shape illustrated in FIG. 3. The batts weigh an average of 26 grams. Water, in the amount of 1.6 grams, is sprayed on the under-surface of the batt. The entire batt is subjected to compression in a contoured press or is calendared with increasing pressure from the central portion to the transverse ends. The pressure increases from the central region to the transverse ends of the batt.

A paper-like gradient densified skin is formed on the surface of the batt to which the water spray is applied. Portions of the batt are removed and tested for density. These portions are designated by the letters A-E in FIG. 2. These densities are shown in Table 1 below. The distances indicated are measured from the center of the batt to the center of the portion removed.

Sample 1 is prepared as discussed above.

Sample 2 is prepared as before with the addition of 5 embossed lines as shown in FIG. 3.

Sample 3 is prepared in the same manner as Sample 2 except that the paper-like skin is formed by substituting 1.2 g of latex emulsion for the water.

Sample 4 is prepared in the same manner as Sample 3 except that 0.6 g of the latex emulsion is used.

A control sample is prepared in the same manner as each of the samples above except the batt is not compressed in the contoured press, but is highly compressed by a flat press or conventional calendaring procedure.

TABLE 1

Density is expressed in gm/cc at 0.16 lb/sq. in. load.

| SAMPLE NO. | PORTION | | | | | CONTROL Average Density |
|---|---|---|---|---|---|---|
| | A 1¼" | B 2¼" | C 3¼" | D 4¼" | E 6" | |
| 1 | 0.040 | 0.043 | 0.048 | 0.058 | 0.079 | 0.063 |
| 2 | 0.062 | 0.068 | 0.080 | 0.093 | 0.100 | 0.074 |
| 3 | 0.058 | 0.065 | 0.069 | 0.078 | 0.087 | 0.073 |
| 4 | 0.056 | 0.062 | 0.074 | 0.086 | 0.100 | 0.068 |

The data in Table 1 clearly show that the density in the samples made in accordance with the present invention increases with distance from the center of the batt.

EXAMPLE 2

The samples prepared in Example 1 are tested to determine the wicking properties and the liquid holding capacity.

The wicking test is performed by separating the batt at the center cross section line into two equal halves. The batt section is then hung in a vertical position with Section E (FIG. 2) at the top. A large Petri dish, containing 1.59% saline solution, is placed on an adjustable stand and is raised to contact the bottom surface of the batt strip. The time necessary for the liquid to wick the distance shown is expressed in seconds.

The liquid holding capacity is expressed in grams of liquid per gram of batt measured after 8 minutes of wicking.

TABLE 2

| SAMPLE NO. | WICKING IN SECONDS | | | | | LIQUID HOLDING CAPACITY g/g |
|---|---|---|---|---|---|---|
| | 1¼" | 2¼" | 3¼" | 4¼" | 6" | |
| Control 1 | 3 | 9 | 19 | 36 | 90 | 5.8 |
| Example 1 | 3 | 8 | 17 | 33 | 81 | 6.8 |
| Control 2 | 3 | 7 | 16 | 28 | 106 | 6.6 |
| Example 2 | 4 | 8 | 16 | 29 | 72 | 7.6 |
| Control 3 | 3 | 9 | 19 | 32 | 104 | 5.8 |
| Example 3 | 3 | 8 | 17 | 30 | 86 | 7.0 |
| Control 4 | 3 | 9 | 20 | 38 | 99 | 6.1 |
| Example 4 | 4 | 9 | 17 | 29 | 71 | 7.3 |

As can be seen from the data above, in each instance wherein the density gradient is present, the liquid wicks faster and the liquid holding capacity is greater.

It will be understood by those skilled in the art that variations and modifications of the specific embodiments described above may be employed without departing from the scope of the invention as defined in the appended claims.

I claim:

1. An absorbent structure comprising an absorbent batt of loosely compacted cellulosic fibers substantially of rectangular shape wherein the longitudinal sides are longer than the transverse ends, said batt having gradient densities whereby the density of the batt increases along a longitudinal line starting from the central portion of the batt to each transverse end, the density in a cross direction being substantially constant on any given line.

2. The absorbent structure of claim 1 wherein the density near the transverse ends of the absorbent structure is at least 1.5 times the density in the central portion of the absorbent structure.

3. The absorbent structure of claim 1 wherein a paper-like gradient densified skin is formed on one surface of the absorbent batt.

4. The absorbent structure of claim 1 wherein densified lines extending from the central portion toward the transverse ends of the absorbent structure are provided.

5. The absorbent structure of claim 4 wherein a paper-like gradient densified skin is formed on one surface of the absorbent batt.

6. A disposable diaper comprising a moisture-permeable facing, an absorbent batt in superposed position to said facing, and a moisture-impermeable backing superimposed on the side opposite the absorbent batt from the facing, said absorbent batt being of loosely compacted cellulosic fibers and having gradient densities whereby the density of the batt increases along a longitudinal line starting from the central portion of the batt to each transverse end, the density in a cross direction being substantially constant on any given line.

7. The disposable diaper of claim 6 wherein a paper-like gradient densified skin is formed on the surface of the batt in contact with the backing.

8. The disposable diaper of claim 6 wherein densified lines extend longitudinally from the central portion of the batt toward each transverse end.

9. A disposable diaper of claim 6 wherein a paper-like gradient densified skin is formed on the surface of the batt in contact with the backing and densified lines longitudinally extending from the central portion toward the transverse ends of the batt are provided.

10. A sanitary napkin comprising a moisture-impermeable backing, an absorbent batt superposed on said backing, and a moisture-permeable covering superposed on said batt on the side opposite the backing, said batt being of loosely compacted cellulosic fibers and having gradient densities whereby the density of the batt increases along a longitudinal line starting from the central portion of the batt longitudinally toward each transverse end, the density in a cross direction being substantially constant on any given line.

11. The sanitary napkin of claim 10 wherein a paper-like gradient densified skin is formed on the surface of the batt in contact with the moisture-impermeable backing.

12. The sanitary napkin of claim 10 wherein densified lines extending longitudinally from the central portion to each transverse end are provided on the absorbent batt.

13. The sanitary napkin of claim 10 wherein a paper-like gradient densified skin is formed on the surface of the batt in contact with the backing and densified lines longitudinally extending from the central portion toward each transverse end of the absorbent batt are provided.

14. A process for preparing an absorbent structure which comprises providing a loosely compacted cellulosic fibrous batt having longitudinal sides longer than the transverse ends and compressing the batt to provide gradient densities whereby the density of the batt increases from the central portion of the batt toward each transverse end.

* * * * *